United States Patent [19]

Doan

[11] 4,312,350
[45] Jan. 26, 1982

[54] APPARATUS FOR COLLECTING SEMINAL FLUIDS

[76] Inventor: Rosetta C. Doan, 4580 Beechnut, Apt. 110 East Court, Houston, Tex. 77096

[21] Appl. No.: 68,897

[22] Filed: Aug. 23, 1979

[51] Int. Cl.$^3$ .............................................. A61M 1/00
[52] U.S. Cl. ...................................... 128/276; 128/79
[58] Field of Search ................ 119/14.5, 14.41, 14.44; 128/79, 276, 277, 278, 294, 295, 297, 300, 38

[56] References Cited

U.S. PATENT DOCUMENTS

| | | | |
|---|---|---|---|
| 1,971,467 | 8/1934 | Scott | 119/14.5 |
| 2,160,651 | 5/1939 | Erling | 119/14.41 |
| 2,686,519 | 8/1954 | Westerman | 128/79 UX |
| 3,631,853 | 1/1972 | Burdette, Jr. | 128/79 |
| 3,910,262 | 10/1975 | Stoughton | 128/79 |

FOREIGN PATENT DOCUMENTS

| | | | |
|---|---|---|---|
| 101841 | 8/1937 | Australia | 128/299 |
| 2606869 | 9/1977 | Fed. Rep. of Germany | 128/279 |

OTHER PUBLICATIONS

"Mechanics and Production of Quality Milk", Noorlander et al, Democrat Printing Co., Madison, WI; 1965, p. 58.

*Primary Examiner*—Robert W. Michell
*Assistant Examiner*—J. L. Kruter
*Attorney, Agent, or Firm*—Bard, Groves, Sroufe, Ryerson & Jackson

[57] ABSTRACT

Method and apparatus for collecting seminal fluid for artificial insemination is provided and wherein the apparatus has a flexible wall closed at one end and with a rim at the other open end movable in a reciprocating fashion back and forth with respect to the closed end wall. An inflatable sphincter member is located within the vagina adjacent the closed end and applies pressure to the penis during thrusting actions by the animal.

14 Claims, 3 Drawing Figures

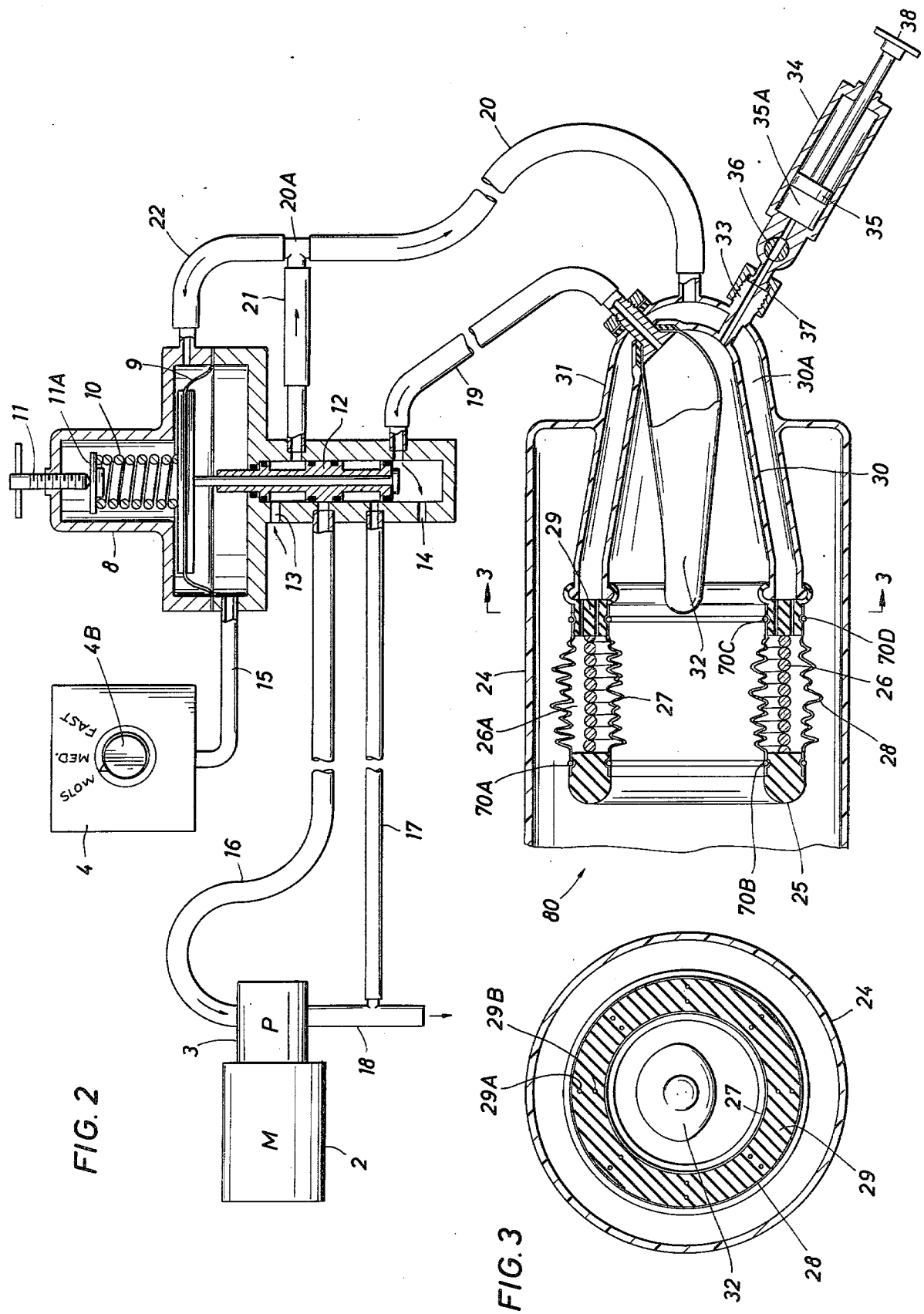

APPARATUS FOR COLLECTING SEMINAL FLUIDS

BACKGROUND OF THE INVENTION

This invention relates to method and apparatus for collecting seminal fluids and more particularly relates to an artificial vagina for collecting semen from animals.

The most common method of collecting semen in animals is by the use of an artificial vagina. This usually consists of a stiff rubber tube having an interior rubber liner which leads to a rubber cone that is connected to a test tube for collecting the semen. The length of the vagina varies but should be long enough so that the penis penetrates completely and ejaculation takes place directly into the cone and test tube. Prior to collection, the vagina is filled with warm water and lubricated internally with an innocuous lubricant such as paraffin or vaseline. The internal temperature of the vagina should be about 45° C. to cover any heat loss prior to actual collection.

It is the usual practice to tease the animal prior to actual collection, and this consists of exciting the animal by allowing him to see and approach the teaser animal and even mounting but without ejaculation taking place. During the teasing, accessory fluid usually dribbles from the prepuce and the animal shows signs of erection. This separation is of considerable importance and unless it is carried out the collection is of poor quality.

The actual technique of collection is also important. It is advisable to apply the artificial vagina to the penis only when the animal is actually probing for it, and obviously prepared for service. It should not be applied as the animal is just mounting or in the process of dismounting, since quite apart from the unsatisfactory psychological effect on the animal, the semen quality and the volume of the ejaculate are inferior.

Great care must be exercised regarding the angle at which the vagina is held and collection taken. Some animals thrust violently against the hindquarters of the teaser, resulting in sharp bending of the penis and the resulting infliction of pain, which if repeated often enough, will inhibit the animal from further service.

The normal pattern of behavior of the animal is to approach the hindquarters of the teaser and nuzzle the base of the tail for a few seconds. The back is then depressed and there is a slight pumping action accompanied by erection and dribbling of accessory fluid. The animal then mounts, dropping his forelegs in front of the external iliacs of the teaser, and the penis begins to probe for the vagina.

At this point, the operator standing to the right of the animal clasps the sheath with his left hand, deflects the penis to one side, and at the same time holds the artificial vagina in his right hand so that entry of the penis takes place normally. The animal will thrust vigorously sometimes leaping off the ground in the process.

The prior art is replete with artificial vaginas that can be used as above described, for example, and as depicted in U.S. Pat. Nos. 2,441,868; 3,421,504; 3,631,853; 3,910,262; and 4,059,100. While these and other artificial vaginas have proved to be satisfactory for the collection of semen in animals, they suffer from the disadvantage of being too rigid during collection and lack the elasticity provided by the vagina of a living teaser during the actual thrust. Such rigidity and lack of elasticity results in a poor quality of collection as compared to the collection produced by a living vagina or an aritifical vagina approaching the characteristics of a living vagina.

These disadvantages of the prior art, and especially the aforementioned U.S. patents, are overcome with the present invention, and commercially acceptable embodiments of an artificial vagina and the like are herein provided which are not only fully capable of collecting seminal materials under most operating conditions but which are also fully capable of other tasks completely beyond the capabilities of the devices of the prior art. More particularly, however, the embodiments of the present invention are capable of controlled operation with a much hiher efficiency.

SUMMARY OF THE INVENTION

This invention is for method and apparatus for collecting seminal fluids and specifically for an artificial vagina for collecting seminal fluids for artificial insemination. The vagina is formed by a flexible elongated tubular member having a closed end for receiving and storing ejaculated semen and an open end having a rim of a diameter sufficient enough to receive the penis of the animal. A vacuum regulator is connected to said tubular member and causes the rim of the vagina to move toward the closed end of the tubular member. A spring within the tubular member returns the rim in a direction opposite the closed end thereby setting up a reciprocating motion of the tubular vagina.

In one particularly ideal embodiment of the present invention, the artificial vagina is formed of two concentric and spaced-apart soft rubber sheaths having located therebetween an annular spring. A hard rubber rim forms the open end of the vagina whereas two concentric hard rubber cones form the semen receptor. A drain is provided in the hard cones where semen collects, and an airtight probe is insertable into the drain for collecting and removing seminal fluid from the vagina and for transferring the semen to suitable dilutors for ultimate storage.

In another ideal embodiment of the present invention, the artificial vagina is provided with a finger-like and inflatable sphincter member located within the vagina and at the closed end thereof. Inflation of the sphincter member during the thrust of the animal adds pressure to the penis in order to assist ejaculation of the semen. The presence of the sphincter member together with the reciprocating action of the vagina simulates more or less the live vaginal action of the teaser during service, and thereby provides a more realistic sensation to the organ of the animal whereby the quality as well as the quantity of seminal fluid collected is substantially increased.

Accordingly, it is a feature of the present invention to provide method and apparatus for collecting seminal fluids and which includes an artificial vagina that more closely assimilates the live vagina of the teaser.

It is another feature of the present invention to provide an artificial vagina that includes flexible walls which are able to be moved in a reciprocating fashion with respect to the penis of the animal in order that the action of a teaser vagina may be produced in the animal.

It is a further feature of the present invention to provide an artificial vagina that moves in a reciprocating fashion on the penis of the animal, and which includes an inflatable sphincter for applying pressure to the animal penis during the thrusting actions.

It is yet another feature of the present invention to provide an artificial vagina that massages the penis of the animal from which semen is to be collected in a fashion that is as natural as possible, that is easy to handle, controllable, and self-driven.

It is a still further feature of the present invention to provide an artificial vagina which is simple, durable, and which may be manufactured and sold at a reasonable cost.

It is also a feature of the present invention to provide an artificial vagina that will develop an erect organ to more effectively produce seminal fluid in greater volume and quality than heretofore possible by more closely assimilating the action of the live vagina of the teaser and without heavy reliance upon the physiological effect upon the animal by the teaser.

These and other features and advantages of this invention will become apparent from the following detailed description, wherein reference is made to the figures in the accompanying drawings.

IN THE DRAWINGS

FIG. 2 is a pictorial representation partly in cross section and similar to FIG. 2 but with the vagina and elements of the vacuum system shown in another position than that depicted in FIG. 1.

FIG. 3 is a side view of the artificial vagina of FIG. 2 and taken along the line 3—3 of FIG. 2.

DETAILED DESCRIPTION

Figure 1:
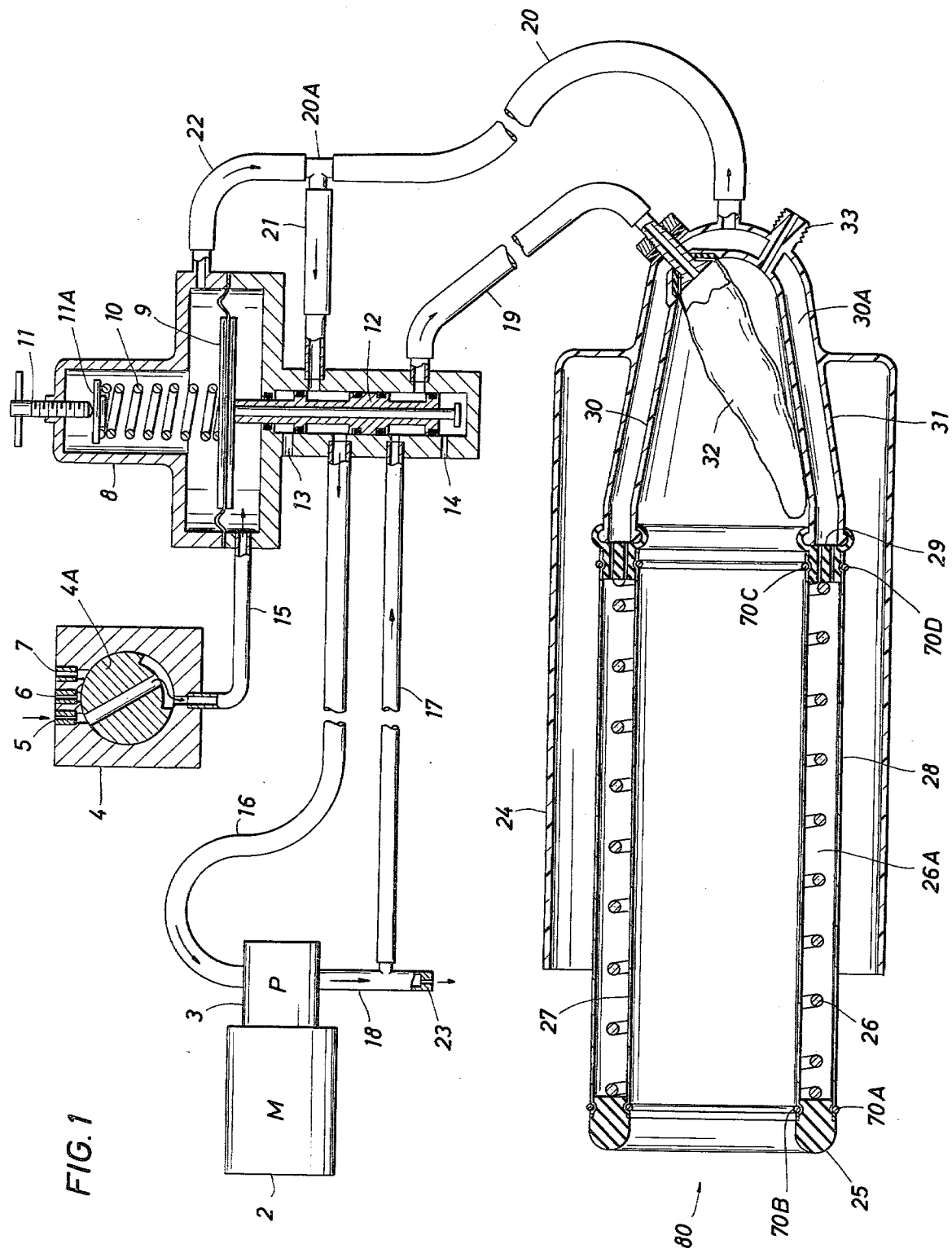
FIG. 1 is a pictorial representation partly in cross section of the artificial vagina of the present invention together with the associated vacuum system for causing movement of the vagina.

With reference to FIG. 1, there will be seen an electric motor 2 for driving a vacuum pump 3. Vacuum pump 3 has a pressure side outlet line 18 containing a flow restrictor 23 that is in communication with the atmosphere. Outlet line 18 also includes a line 17 extending to spool valve 12. Line 16 is connected between the spool valve 12 and the vacuum side of the pump 3.

Spool valve 12 includes two vents 13 and 14 in order to provide flow communication with the atmosphere as described hereinafter. Thus as seen in FIG. 1, the position of the spool valve 12 connects lines 16 and 21, and lines 17 and 19, respectively. In the other position of the spool valve 12 as seen in FIG. 2, however, valve 12 connects lines 19 and 21 to the atmosphere via ports 13 and 14, while blocking lines 16 and 17 altogether.

Connected to the top of the spool valve 12 is a diaphragm 9 which is biased by spring 10 located within the housing 8 of the vacuum regulator. Set screw 11 of the vacuum regulator 8 is used to increase or decrease the bias of the spring 10 acting on the diaphragm 9. A flow restriction valve 4 communicates with one side of diaphragm 9 via line 15, and ports 5, 6, and 7 communicate to the atmosphere. Port 5 is the smallest in diameter and corresponds to the "slow" setting seen in FIG. 2. Port 7 is the largest diameter port of the three and corresponds to the "fast" setting seen in FIG. 2. Port 6 is of medium diameter and corresponds to the "medium" setting of FIG. 2. Thus, in FIG. 1, it should be apparent that valve member 4A may be positioned to connect line 15 with either of ports 5-7 by rotating the knob 4B of FIG. 2.

The connector 20A in FIG. 1 communicates lines 21 and 22 with line 20 which leads in turn to the artificial vagina shown generally at 80. All of the various lines 15-22 may be of plastic tubing but conventional rubber vacuum tubing of thick walled construction is preferred.

Vagina 80 will be seen to comprise a housing 24 of stiff rubber or plastic material and which is intended to function as a handle for the operator to grasp when the vagina is in the process of being placed about the penis of the animal intended for the collection of semen. In any event, the vagina itself is of tubular soft rubber construction and consists of an inner first sheath 27 and an outer second sheath 28.

Rim 25 is disposed between and connected to sheaths 27 and 28 in an airtight seal by a pair of compression rings 70A and 70B. Rim 25 is of harder rubber than are sheaths 27 and 28 and should be of a diameter to fully accept the penis of the animal whose semen is to be collected. A pair of hard rubber inner and outer cones 30 and 31 form the closed end of the vagina, and the sheaths 27 and 28 are connected to the cones 30 and 31 by means of a vented ring 29 including inner and outer compression elements 70C and 70D. As shown in FIG. 3, ring 29 includes therein various vents 29A and 29B which provide communication between the cone chamber 30A and the sheath chamber 26A.

Disposed in the sheath chamber 26A and extending from the rim member 25 to the ring member 29 is a coiled spring 26. The spring 26 is shown in its normal position in FIG. 1, and in its compressed position in FIG. 2. As will be explained in more detail hereinafter, the vagina is alternately compressed as in FIG. 2 and expanded as seen in FIG. 1. The primary function of the coiled spring 26 is to return the vagina to its extended position as seen in FIG. 1. The vacuum assembly causes the compression of the vagina as depicted in FIG. 2.

In any event, and again with reference to FIG. 1, the vagina includes an elongated finger-like and inflatable sphincter member 32 located adjacent the inner cone 30 and in communication with the spool valve 12 via line 19. Member 32 is of soft rubber as are sheaths 27 and 28, and when inflated as seen in FIG. 2, compresses gently the penis of the animal within the sheath 27 to further stimulate the animal to ejaculate.

Inner cone 30 includes at one end a drain 33 for removing collected seminal liquid. Since semen is sensitive to the atmosphere, it may be withdrawn from cone 30 by a probe 34 as depicted in FIG. 2 having a piston 35 which when moved away from valve 36 by handle 38 will draw semen into chamber 35A. Valve 36 can then be closed to effectively isolate the semen in chamber 35A from the atmosphere. Collar 37 can then be disconnected from drain 33 and the probe 34 sent to the laboratory where the semen may be mixed with dilutors and stored for future use.

In operation, motor 2 is actuated which drives vacuum pump 3. A vacuum is drawn in line 16 which is transmitted to cone chamber 30A by lines 20 and 21 as seen in FIG. 1. Thus, spool valve 12 is in position to connect lines 16 and 21 as will be seen therein. At the same time, pressure in line 18 is partially vented at restriction 23 but with the remainder conducted in line 17 through spool valve 12 and into line 19. Thus, the sphincter 32 is in the process of being inflated, all as shown in FIG. 1.

In addition to drawing a vacuum in chamber 30A, pump 3 also draws a vacuum on diaphragm 9 via line 22. Thus, as seen in FIG. 1, diaphragm 9 will have a tendency to move upwardly against the bias of spring 10. Concurrently, however, line 20 allows a vacuum to exist in chamber 30A and since ring 29 is vented, the sheath chamber 26A is also put under a vacuum. This tends to move the ring 25 to the right as seen in FIG. 1 toward ring 29, and against the bias of spring 26. Thus, in FIG. 1, the sheath 27 and 28 is tending to be compressed to the state shown in FIG. 2, while the member 32 is tending to be inflated as seen in FIG. 2.

When the vacuum in line 22 as seen in FIG. 1 is sufficient to overcome the spring bias of coil 10, diaphragm 9 will move upwardly to shift spool valve 12 to the position shown in FIG. 2. The vagina of FIG. 1 will compress to the position of FIG. 2, and the deflated sphincter 32 of FIG. 1 will be inflated as seen in FIG. 2.

With reference now to FIG. 2, spool valve 12 will vent line 19 via port 14 to deflate member 32. At the same time, spool valve 12 will vent lines 20, 21, and 22, via port 13 which results in the extension of spring 26 back to its position as seen in FIG. 1, and the fall of diaphragm 9 to the position shown in FIG. 1.

Thus, the cycle will repeat again, with valve 12 shifted from the vent position of FIG. 2 back to the vacuum applicator position of FIG. 1. Member 32 will then begin to inflate again whereas the vagina will tend to contract again. It should be apparent that the amount of vacuum required to move the diaphragm 9 to the upward position of FIG. 2 is regulated by the pressure on plate 11A applied to spring 10 by set screw 11. Similarly, the speed of the cycling of the elements as seen in FIGS. 1 and 2, thus inflation-deflation of member 32 and extension-retraction of the vagina 27, 28 can be increased or decreased by valve 4. Thus, a slow cycle is caused when valve 4A connects vent 5 and line 15, whereas a fast cycle is produced when valve 4A connects vent 7 with line 15.

With reference now to the collection of semen from a bull for example, and as noted hereinbefore, the inner sheath 27 and the rim 25 are swabbed with vaseline after having been emptied of hot water. The bull is led to approach the rear of the teaser and to mount the teaser at which time the bull probes for the vagina of the teaser with a full erection. The operator deflects the penis to one side with his left hand, and with his right hand on the housing 24, directs the penis into rim 25 and into the inner sheath 27 and against member 32 and inner cone 30. Motor 2 is then actuated and the artificial vagina 80 is caused to retract and expand with rim 25 moving along the erect penis of the bull. The bull will thrust viorously, sometimes leaping off the ground, and such thrusting action will drive the penis of the bull deeper into the cone 30 and against the alternately inflating and deflating sphincter member 32. The sphincter member 32 and the movement of the rim 25 to and fro simulate the action of the vagina of the live teaser with the result that vastly improved specimens of semen are possible with the vagina of the present invention. The bull ejaculates into the inner cone 30 and soon dismounts the teaser animal, at which time the vagina 80 is removed from the penis of the bull and held in a fashion to drain the collected semen toward outlet 33. Probe 34 is then used as above described to collect the semen and to transfer it to the laboratory for further treatment.

The vagina of the present invention is considered to be more efficient than those artificial vaginas known heretofore and this is attributed to the ability of the hereindescribed vagina to move in a reciprocating fashion over and with respect to the erect penis of the animal from which seminal fluid is to be collected. This is to be contrasted with those other devices of the prior art which are more or less stationary and which act as collectors only. It is considered that the reciprocating motion of the vagina of the present invention together with the action of the sphincter member 32, will not only effectively collect semen but induce a better ejaculate from the animal because of the similarity of the artificial vagina of the present invention to the live vagina of the teaser for example, with the result physiological effects in animals are enhanced.

The artificial vagina of the present invention is particularly useful in the collection of semen for breeding operations in domestic animals particularly dairy cattle. This is because it enables many more females to become impregnated by a male of outstanding genetic worth, for example a proven bull, one which has already bred daughters producing high milk yields. Artificial insemination has also proved useful in preventing the spread of certain venereal diseases such as dourine in horses and trichomonas infection in cattle. Another use is for making crosses between animals belonging to varieties in which the disparity in size is so great that coitus between them is difficult or impossible. Crosses can also be made between different species where there is difficulty in getting normal mating to take place.

The term animal as used hereinabove is generally intended to cover creatures such as bulls, stallions, boars, rams, and dogs, for example, however, it should be understood that it is not so limited and that the apparatus and methods referred to herein can, if desired, be applied to the male homo sapiens.

Referring again to FIG. 1, while not shown for the sake of clarity, drain 33 can include a cap to close the drain 33 to prevent leakage of semen therefrom. The cap is removed after the animal ejaculates, and as seen in FIG. 2, probe 34 is then insertes into the drain 33 to remove the collected semen. It should also be noted that while sheaths 27 and 28 are shown connected to rim 25 and ring 29 by a series of compression members 70A–70D, the sheaths 27 and 28 could be formed integrally with the rim 25 and ring 29, if desired.

While it is not the purpose herein to deal with techniques after collection, it can be said that the semen in probe 34 is delivered to a laboratory where it is diluted for purposes of preservation and to avoid any depletion of sperm survival. This is normally accomplished by mixing the collected semen with a dilutor, so called, the function of which is to increase the volume of the sperm-containing liquid in order to multiply the number of doses which can be made available from a given semen sample, to prevent temperature shock, to preserve the spermatozoa for long periods with a minimum fall in fertility, and to have a buffering effect. Typical of such dilutors are for example, egg yolk, mixtures of egg yolk with glycine or various citrates and phosphates, and milk including skimmed milk, homogenized whole milk, milk containing egg yolk, glycine and glycerol, powdered milk, and even cream. Antibiotics such as sulfanilamide, penicillin, and streptomycin may also be added. In any event, after the collected semen has been diluted, with whatever dilutor is chosen, it is then cooled and frozen in order to maintain fertility for as long a period as is possible. Thus, the diluted and cooled semen may be stored frozen in solid carbon dioxide at $-79°$ C., or in liquid nitrogen at $-193°$ C. Only slight differences have been found between fresh and frozen semen, and semen frozen for up to twelve months has been found effective when animals were inseminated.

As noted hereinabove, a live teaser animal on which the animal mounts is used to collect semen. In the case of a bull, a cow may be used, or a bullock or one of the other bulls standing at stud. Once a bull is conditioned for service, however, there is little difference in erotic effect whether the teaser is a cow, bullock, or bull. One advantage of the use of a male teaser is that there is no possibility of accidental service and the risk of spread of veneral disease is practically eliminated. The use of a dummy teaser is possible although not wholly satisfactory because of psychological difficulties induced in the bull.

In any event, if a live teaser is selected, it must be an animal which will stand quietly during the process of collection. As in the case of the bull, stallions can be trained to mount mares or even a dummy mare. Boars are easily trained to use a sow dummy while rams are not and seem to prefer an ewe or another ram. Neither a teaser bitch nor a dummy are required for a dog but collection is possible if initiated by digital manipulation followed by application of the artificial vagina.

It should be apparent that the size of the artificial vagina of the present invention will vary from animal to animal depending of course upon the size of the penis of the animal from which semen is to be collected, and particularly with a view towards accommodating fully the volume of the ejaculate to be expected to be collected. For example, the average volume of ejaculate varies from species to species, and low volumes are produced by bulls and rams on the order of 1-5 c.c.'s, while in the case of stallions and boars, volumes in the range of 50-250 c.c.'s can be expected.

It should be noted that while the sphincter member 32 is shown in FIG. 1 as terminating just short of ring 29, the member 32 may be of any length desired. For example, member 32 can be of a length to reach rim 25 in either of the extended position of the rim 25 as seen in FIG. 1, or in the compressed position of the rim 25 as seen in FIG. 2. Of course, it could also extend through and beyond the rim 25 as seen in either of FIGS. 1 and 2.

It will be apparent from the foregoing that many other variations and modifications may be made in the structures and methods described herein without departing substantially from the essential concepts of the present invention. Accordingly, it should be clearly understood that the particular and specific forms of the invention described herein and depicted in the accompanying drawings are exemplary only and are not intended as limitations of the scope of the present invention.

What is claimed is:

1. An apparatus for collecting seminal fluids and the like, comprising:
    an outer housing member,
    a flexible elongate tubular member positioned at least partially within said housing member and having a closed end and a rim defining an open end opposite said closed end,
    vacuum regulator means for causing said rim to move from a first position to a second position toward said closed end of said tubular member,
    vacuum pump means in fluid communication with said vacuum regulator means,
    restoring means for returning said rim from said second position to said first position,
    a drain in said closed end of said tubular member, and
    semen collector means adapted for fluid communication with said drain for removing seminal fluids from said closed end of said tubular member, said semen collector means including a semen chamber, a piston slidable within said semen chamber, and valve means for selectively isolating said semen chamber from the atmosphere.

2. The apparatus of claim 1, wherein said tubular member includes first and second spaced-apart sheaths, and wherein said restoring means includes a coiled spring interposed between said sheaths.

3. The apparatus of claim 2, wherein said rim closes one end of each of said sheaths to form a fluid chamber, and wherein said vacuum regulator means is connected to said fluid chamber at the other end of said sheaths.

4. The apparatus of claim 3, further comprising:
    said vacuum regulator means including a spool valve for alternately providing communication between said fluid chamber and the vacuum side of said pump means, and between said fluid chamber and the atmosphere.

5. The apparatus of claim 1, further comprising:
    a flexible and inflatable member located adjacent said closed end of said tubular member and in fluid communication with said regulator means.

6. The apparatus of claim 5, further comprising:
    said vacuum regulator means including a spool valve for alternately providing communication between the pressure side of said pump means and said inflatable member, and between said inflatable member and the atmosphere.

7. A massaging apparatus adapted for stimulating a male genital organ, comprising:
    an outer housing member,
    an outer flexible sheath positioned at least partially within said housing member and having a first movable end portion,
    an inner flexible sheath substantially enclosed within said outer sheath and having a second movable end portion,
    a rim connecting said first and second end portions and movable relative to said housing member for sliding engagement with said organ,
    power means for causing said rim to move from an extended position to a retracted position,
    restoring means for returning said rim from said retracted position to said extended position, and
    a flexible inflatable member disposed within said housing member and adapted for engagement with said organ and movable relative to said rim and said housing member.

8. The apparatus of claim 7, wherein said outer and inner flexible sheaths and said rim form a fluid chamber, and wherein said power means includes fluid pressure regulator means in fluid communication with said fluid chamber.

9. The apparatus of claim 8, wherein said inflatable member is in fluid communication with said fluid pressure regulator means.

10. The apparatus of claim 9, wherein said vacuum regulator means selectively controls movement of said rim and movement of said inflatable member.

11. The apparatus of claim 8, wherein said restoring means comprises a coiled spring interposed between said outer sheath and said inner sheath.

12. The apparatus of claim 7, further comprising:
    a semen receptacle connected to a stationery end of said inner flexible sheath, and
    semen collector means adapted for fluid communication with said receptacle for removing seminal fluids from said receptacle, said semen collector means including a semen chamber for storing a quantity of seminal fluids and valve means for selectively isolating said semen chamber from the atmosphere.

13. An apparatus for collecting seminal fluids, comprising:
   an outer housing member,
   a flexible elongate tubular member positioned at least partially within said housing member and having a closed end a rim defining an open end opposite said closed end,
   vacuum regulator means for causing said rim to move from a first position to a second position toward said closed end of said tubular member,
   restoring means for returning said rim from said second position to said first position, and
   semen collector means adapted for fluid communication with said closed end of said tubular member, said semen collector means including a semen chamber, a piston slidable within said semen chamber for removing seminal fluids from said closed end of said tubular member, and valve means for selectively isolating said semen chamber from the atmosphere.

14. The apparatus of claim 13, wherein said tubular member includes an outer sheath and an inner sheath, and wherein said restoring means includes a coiled spring interposed between said sheaths.

* * * * *